US00PP17272P2

(12) United States Plant Patent
Heims

(10) Patent No.: US PP17,272 P2
(45) Date of Patent: Dec. 12, 2006

(54) ***EUPHORBIA* PLANT NAMED 'ORANGE GROVE'**

(50) Latin Name: *Euphorbia amygdaloides 'Rubra'* × *Euphorbia amygdaloides var. robbiae*
Varietal Denomination: Orange Grove

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/171,583

(22) Filed: Jun. 29, 2005

(51) Int. Cl.
*A01H 5/00* (2006.01)

(52) U.S. Cl. ..... Plt./302
(58) Field of Classification Search ..... Plt./302
See application file for complete search history.

(56) References Cited

PUBLICATIONS http://www.plantdelights.com/Catalog/Current/Detail/06182.html "*Euphorbia amygdaloides* 'Orange Grove' PPAF" Apr. 11, 2006.* http://www.terranovanurseries.com/wholesale/modules.php?name=Content&pa=showpage&... "*Euphorbia amydaloides* 'Orange Grove' PPAF PVR" pp. 1–2 Apr. 11, 2006.*

* cited by examiner

*Primary Examiner*—Wendy Haas
(74) *Attorney, Agent, or Firm*—Klarquist Sparkman, LLP

(57) ABSTRACT

A new and distinct cultivar of *Euphorbia amygdaloides* plant characterized by deep green leaves with red new growth and stems, large chartreuse inflorescences that turn orange in the summer, and a rhizomatous habit.

1 Drawing Sheet

Botanical denomination: *Euphorbia amygdaloides* 'Rubra'×*Euphorbia amygdaloides* var. *robbiae.*
Variety designation: 'Orange Grove'.

BACKGROUND OF THE INVENTION

The present invention relates to a new and distinct cultivar of a hardy, suffrutescent perennial of the genus *Euphorbia*, known by the cultivar name of 'Orange Grove'. The genus *Euphorbia* is a member of the family Euphorbiaceae.

The new cultivar originated as a garden cross between a *Euphorbia amygdaloides* 'Rubra', an unpatented plant as the seed parent, and *Euphorbia amygdaloides* var. *robbiae*, an unpatented plant, as the pollen parent.

SUMMARY OF THE INVENTION

This new cultivar is characterized by:

1) Red tinted new leaves growing into deep green leaves.
2) Red purple stems.
3) Rhizomatous habit like pollen parent, *Euphorbia amygdaloides* var. *robbiae.*
4) Large inflorescence size.
5) Bracts, which turn from lime green to orange with maturity.
6) Excellent vigor, rapid growth.

Asexual propagation by tip cuttings using standard propagation techniques with terminal shoots as done in Canby, Oreg., shows that the foregoing characteristics and distinctions come true to form and are established and transmitted through succeeding propagations. This new cultivar has been reproduced only by asexual propagation (cuttings). Each of the progeny exhibits identical characteristics to the original plant. The present invention has not been evaluated under all possible environmental conditions. The phenotype may vary with variations in environment without a change in the genotype of the plant.

BRIEF DESCRIPTION OF THE DRAWING

The photograph shows a three-year-old *Euphorbia amygdaloides* 'Orange Grove' growing in the ground in May in Canby, Oreg.

DETAILED PLANT DESCRIPTION

The following is a detailed description of the new *Euphorbia* based on observations of two-year-old specimens grown in the ground in full sun under typical outdoor conditions in the trial garden in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Evergreen perennial, flowering on one year old stems.
- *Form.*—Upright and rhizomatous.
- *Hardiness.*—USDA Zone 7 to 9.
- *Size.*—30 cm to 40 cm tall to top of the foliage and 30 cm wide.
- *Vigor.*—Excellent.

Stem:
- *Type.*—Upright, tufted stems which are leafy the first year and flowering the second year.
- *Size without inflorescence.*—Grows to 30 cm tall and 6 mm wide.
- *Internode spacing.*—Variable, further apart at base of the stem, 2 cm to 5 mm.

*Surface.*—Villous.
*Color.*—Greyed Purple 187B.

Leaf:
*Type.*—Simple.
*Arrangement.*—Rosette or alternate.
*Shape.*—Oblanceolate.
*Venation.*—Pinnate.
*Margins.*—Entire, slightly revolute.
*Apex.*—Acute.
*Base.*—Attenuate.
*Blade size.*—5 cm to 6.3 cm long and 1.7 cm to 2 cm wide.
*Texture.*—Leathery, soft, villous on bottom side, glabrous on top side.
*Petiole size.*—2 mm to 12 mm long and 2 mm wide.
*Petiole color.*—Yellow Green 145A to B on top with red, Greyed Purple 183C on underside on new leaves.
*Leaf color.*—Topside — Mature leaves are deep green, closest to Green 137A but darker. New leaves are Green 137A with a brown blush, Brown 200B. Bottom side — Mature leaves are closest to Yellow Green 147A. New leaves are maroon, Greyed Purple 187B.

Inflorescence:
*Type.*—Terminal pseudocyme, pseudoumbellate at tip.
*Number of pedicels.*—20 to 30 per pseudocyme.
*Peduncle.*—Height — 17 cm on edges of clump to 28 cm in middle of the clump. Diameter — 5 to 6 mm. Color — Greyed Purple 187B. Surface texture — Villous. Leaves — At base of each pedicel, oblong, from 35 mm long and 12 mm wide.
*Pedices.*—Length — 5 cm. Surface — Sparsely villous. Color — Greyed Purple 183B.

Bracts:
*Number of bracts per pedicel.*—1.
*Description.*—Connate perfoliate, two-lobed.
*Size.*—30 mm wide and 23 mm high.
*Color.*—Chartreuse, Yellow Green 144A on edges and 154B towards the middle, with maturity they turn orange, Greyed Orange 172B.

Cyathium:
*Description.*—2, on stalks from nectary in middle of the bract, each bract cup containing one stalked female, surrounded by a nectary and with five groups of males. Cyathia with 4 prominent lime green nectar glands (crescent shaped).
*Bract cup description.*—Bowl-shaped, 2 lobed, 8 mm to 9 mm wide and 7 mm deep, chartreuse in color, Yellow Green 145A.
*Description of nectar glands.*—4 prominent, crescent shaped, lime green (Yellow Green 144A), as a unit they are 7 mm across and 4 mm wide.
*Pistil.*—Glabrous, 4 mm long, Yellow Green 144A overall, style 2 mm long.
*Bloom period.*—April to June in Canby, Oreg.
*Fragrance.*—None.

Fruit: None formed. The plant is sterile, no viable fruit is formed.

Seed: None.

Disease problems: None observed. Most *Euphorbia* have problems with root rot (if grown in heavy, wet soils). No mildew has been observed in 4 years on the mother plant of the new variety. No root rot problems have been observed.

Pest problems: No pest problems have been observed outdoors with spider mites or mealy bugs, the most likely problems.

COMPARISONS TO SIMILAR *EUPHORBIA*

Compared to its pollen parent, *Euphorbia amygdaloides* var. *robbiae*, which it most closely resembles, *Euphorbia amygdaloides* 'Orange Grove' has darker green leaves with red new growth rather than green new growth. The flowering stems are red or red tinged rather than green and the flowers are larger and more colorful. They both are rhizomatous and tolerate sun or shade in almost any soil with good drainage.

I claim:

1. A new and distinct cultivar of *Euphorbia amygdaloides* plant substantially as shown and described.

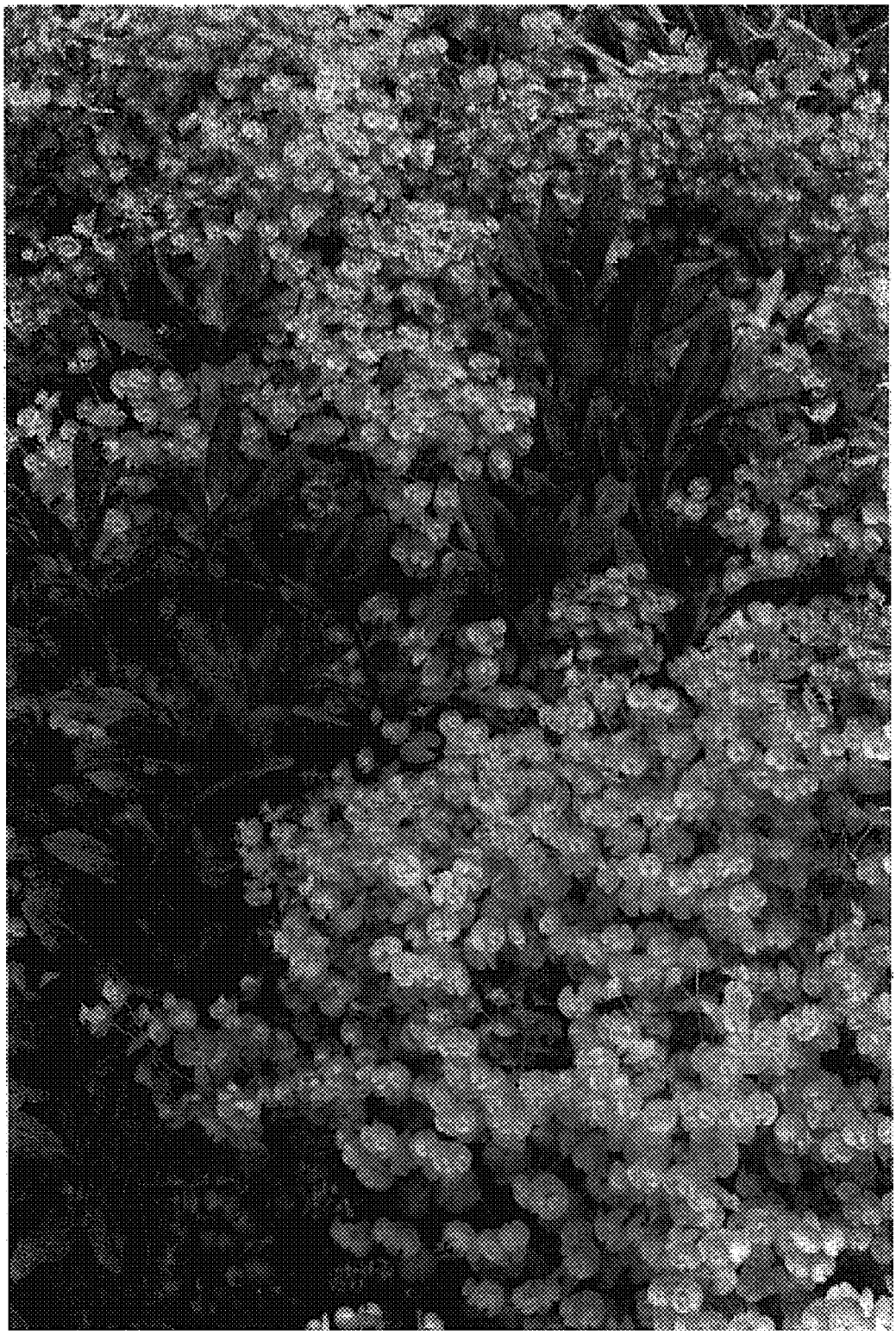

* * * * *